United States Patent [19]
Izatt et al.

[11] Patent Number: 4,755,678
[45] Date of Patent: Jul. 5, 1988

[54] SIMULTANEOUS MEASUREMENT OF MOISTURE CONTENT AND BASIS WEIGHT OF PAPER SHEET WITH A SUBMILLIMETER LASER

[75] Inventors: Jerald R. Izatt, Northport, Ala.; Russell Boulay; Richard Gagnon, both of Cap-Rouge, Canada; Bernard Drouin, Ste-Foy, Canada

[73] Assignee: The University of Alabama, Tuscaloosa, Ala.

[21] Appl. No.: 78,030

[22] Filed: Jul. 28, 1987

Related U.S. Application Data

[63] Continuation of Ser. No. 731,020, May 6, 1985, abandoned.

[51] Int. Cl.$^4$ ............................................. G01N 21/39
[52] U.S. Cl. ................................ 250/358.1; 250/339; 250/359.1
[58] Field of Search ................ 372/4; 250/339, 336.1, 250/358.1, 359.1

[56] References Cited

U.S. PATENT DOCUMENTS

| | | | |
|---|---|---|---|
| 3,551,678 | 12/1970 | Mitchell | 250/341 |
| 3,806,730 | 4/1974 | Tirkkonen et al. | 250/341 |
| 4,427,889 | 1/1984 | Müller | 250/339 |

OTHER PUBLICATIONS

Boulay et al, "Paper Sheet Moisture Measurements in the Far Infrared", Eighth International Conf. on Infrared and Millimeter Waves", Dec. 1983.

Primary Examiner—Carolyn E. Fields
Attorney, Agent, or Firm—Oblon, Fisher, Spivak, McClelland & Maier

[57] ABSTRACT

A system for detecting simultaneously the moisture content and basis weight of paper is disclosed utilizing a submillimeter laser source of radiation of two different wavelengths which is subsequently scanned across the face of the paper. A plurality of detectors placed on the side of the paper opposite the laser supplies the transmittance information for each of the wavelengths to a microcomputer which in turn calculates the moisture content and the basis weight of the material. The two different wavelengths of submillimeter radiation are produced by either a pair of submillimeter lasers pumped by a continuous wave $CO_2$ laser or by a single submillimeter laser pumped by a waveguide type continuous wave $CO_2$ laser whose output is controlled by a piezoelectric crystal tuned resonator in order to provide the required two separate wavelengths alternating in time which are output in the single beam of the submillimeter laser.

5 Claims, 2 Drawing Sheets

SIMULTANEOUS MEASUREMENT OF MOISTURE CONTENT AND BASIS WEIGHT OF PAPER SHEET WITH A SUBMILLIMETER LASER

This application is a continuation of application Ser. No. 731,020, filed on May 6, 1985, now abandoned.

BACKGROUND OF THE INVENTION

1. Field of the Invention

The present invention relates to the on-line measurement of the moisture content of paper sheet at various stages of its manufacture as well as the on-line measurement of the basis weight of the paper.

2. Discussion of Background

The moisture content measurement of sheet paper in the prior art generally falls into the categories of microwave and infrared moisture gauges which can be used for real-time, on-line measurement. Each of the microwave and infrared moisture gauges used in the prior art have several deficiencies common to the type of structure used.

Poor spatial resolution and inadequate accuracy at moisture levels of less than 10% are serious disadvantages to the use of microwave devices. The second and more popular of the currently employed moisture content gauges uses infrared radiation which is usually produced by a filtered thermal source. These devices are more accurate than the microwave gauges because they use two wavelengths produced by alternating transmission filters in front of the source. One of these wavelengths is much more strongly absorbed in water than the other wavelength and from the use of these two wavelengths a fairly reliable water content measurement is possible. It is to be noted, however, that adequate results from using infrared gauges are often difficult to obtain because of the significant IR (infrared) scattering and poor penetration in heavier stock paper. It is also to be noted that the use of infrared gauges is confined to low moisture levels. Since the IR radiation is not confined to a well defined beam as laser radiation is, it is difficult, if not impossible, to steer the radiation for purposes of scanning a significant width of material as the sheet passes rapidly through the newsprint plant machines at up to 90 kilometer per hour. As a consequence, mechanical scanning of the whole device is required. An example of one type of infrared gauge structure is shown by the U.S. Patent to Brunton, U.S. Pat. No. 3,405,268 which illustrates the use of three different wavelengths of infrared radiation in the 1 to 10 micron range in order to measure moisture content and basis weight of paper as well as other dielectric sheet materials. This exemplary showing of an infrared gauge has all the drawbacks mentioned above including its use being confined to light stock paper and to paper which has low moisture levels. Likewise this gauge produces radiation which cannot be steered in order to provide adequate scanning of the width of the paper as it moves through the machines, and hence mechanical displacement of the whole device is required in order to produce the scan.

Neither the microwave nor the infrared type gauges are able to produce a beam in which the radiation is confined and which can be steered, as a laser beam for example, in order to provide fast, accurate, high spatial resolution, and wide range of moisture content measurements over a wide range of dry stock paper material.

There has been a recent attempt to provide for only the moisture measurement of a thin paper sheet using a laser as reflected by "Paper Sheet Moisture Measurements in the Far Infrared" Conference Digest, Eighth International Conference on Infrared and Millimeter Waves by Boulay et al, December, 1983. The theoretical discussions were confined to the use of a single wavelength metallic guided-wave $CH_3OH$ laser with a hole coupled end mirror which is pumped with a $CO_2$ laser whereby the output of the laser is directed at normal incidence onto a immobile paper sheet. This theoretical discussion provide only a measurement of a single wavelength with a quasi continuous wave laser output. This approach with respect to using the hole coupled end mirror arrangement on the output of the $CH_3OH$ laser spreads the laser beam by diffraction and makes it extremely difficult to use for scanning across a width of material as is necessary in machine paper production operations.

SUMMARY OF THE INVENTION

Accordingly, it is an object of the present invention to provide a submillimeter laser system for simultaneously determining the basis weight and moisture content of paper sheet materials in a real-time, on-line measurement system as the paper is produced or fed through a system.

It is another object of the invention to provide a moisture content and basis weight measurement of paper sheet which has capability of scanning a wide sheet of paper quickly and with extreme accuracy for a wide range of moisture content of the paper and which will produce a high-resolution spatial profile of both the basis weight and the moisture content.

The objects of the present invention are attained by utilizing a line-tunable, frequency stabilized optically pumped submillimeter (SMM) laser device which outputs two different wavelengths in the submillimeter range with the output of the laser being fed to an opto-mechanical device which steers the laser beam for scanning of a fed paper sheet. An array of detectors detects the energy transmitted through the paper sheets from the scanned beam and outputs the transmittance information to a microcomputer in order to calculate both the basis weight and the moisture content of the paper sheet.

It is another object of the present invention to provide for multiple wavelengths by utilizing a plurality of submillimeter laser set-ups in conjunction with a beam splitter and a pair of detectors at each of the scanned locations in order to take into account the two separate wavelengths being generated by the two separate submillimeter laser systems.

It is another object of the invention to provide for the generation of two wavelengths by utilizing a waveguide $CO_2$ continuous wave laser in conjunction with a servo controlled piezoelectric mirror displacer which is used in order to generate alternately the two wavelengths necessary for measurement.

It is also an object of the invention to provide that the scanning beam caused by the opto-mechanical device be fed into a plurality of waveguides before being applied to the paper sheet at the various measurement points each normal to the paper.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
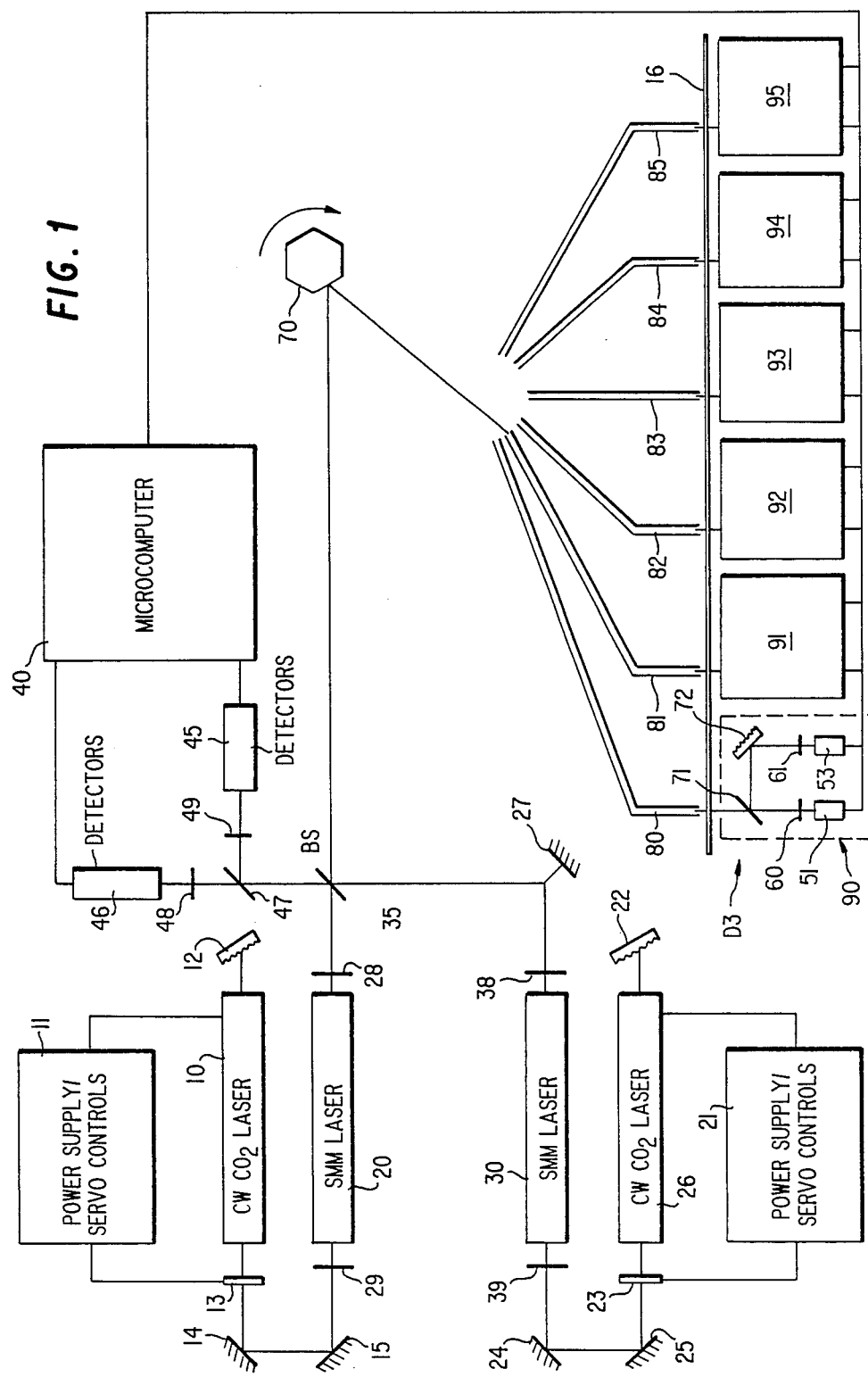
FIG. 1 illustrates a first embodiment for the production and measurement of moisture content and basis weight of paper.

Referring now to the drawings, wherein like reference numerals designate identical or corresponding parts throughout the several views, and more particularly to FIG. 1 thereof, there is illustrated an apparatus for measuring the transmittance and subsequently the moisture content and basis weight of a paper sheet 16 which is output from a paper making machine (not shown) and whose motion is directed out of FIG. 1 towards the reader. The energy eventually directed onto the paper sheet is generated by the two identical submillimeter lasers 20 and 30. Each of the submillimeter lasers 20 and 30 is pumped by the respective CW (continuous wave) $CO_2$ lasers 10 and 26 through plane mirror pairs 14, 15, and 24, 25. Each of the continuous wave $CO_2$ pumping lasers are tuned to one of their output lines in order to generate specific wavelengths by adjustment of the angular orientation of the diffraction gratings 12 and 22 respectively. The frequency of the laser output of the lasers 10 and 26 is then stabilized by servo control of the output couplers 13 and 23, which are mounted on a piezoelectric crystal. The power supply/servo controls 11 and 21 function to provide the necessary power and the electronics for the servo control of the couplers 13 and 23, respectively. This output coupling arrangement 13 and 23 assures sufficient stability of the SMM laser output power to achieve better than 0.5% accuracy in subsequent measurements.

The wavelength of each of the SMM lasers 20 and 30 is determined by the combination of the gas used in the SMM lasers and the chosen wavelength of the continuous wave $CO_2$ lasers 10 and 26. The continuous wave lasers 10 and 26 provide for a continuous scanning output from the SMM lasers 20 and 30 and also provide for precise intensity and frequency control from the output of the SMM lasers. Each of the lasers 20 and 30 have associated therewith a pair of hybrid mirrors 28, 29, and 38, 39, respectively which maintain the beam-structure and quality of the output of the lasers 20 and 30. Each of the hybrid mirrors 28, 29, 38 and 39 is a metallic grid of dimensions appropriate for SMM reflection applied over a dielectric film structure appropriate for 10 micron ($CO_2$) reflection, with both of these structures supported by a transparent crystal.

The output of the submillimeter laser 20 fed through the hybrid mirror 28 enters beam splitter 35 directly while the output of the submillimeter laser 30 is directed by the plane mirror 27 onto the beam splitter 35.

In order to monitor the power output of each of the lasers 20 and 30, a pair of detectors 45 and 46 are utilized in conjunction with a second beam splitter 47. Two detectors are necessary because of the different wavelengths produced by each of the lasers 20 and 30 which result in a need to know the power generated at each of the two wavelengths. In order to provide for proper selection of the same wavelength at all times by the same detector either 45 or 46, a filter 48 is placed before the detector 46 which filters out a first wavelength and passes a second wavelength type radiation whereas the filter 49 in front of the detector 45 passes the first wavelength radiation and filters out the second wavelength radiation. The outputs of the detectors 46 and 45 are fed to the microcomputer 40 in order to serve as a power indication of the output of each of the lasers. The use of this power measurement will be discussed later in conjunction with the calculation that the microcomputer must perform in order to provide the consequent moisture content and basis weight indications.

The other output from the beam splitter 35 is fed to a rotating mirror 70 or other opto-mechanical device which provides for steering of the laser beam which now represents the output from both lasers 20 and 30 at two separate wavelengths. The rotating mirror 70 provides for a scanning of the subsequent beam through the various waveguides 80–85 onto the paper sheet 16. Thus, half of the output of the lasers 20 and 30 passes through the beam splitter 35 and is directed onto the upper end of the waveguides 80–85 by the rotating mirror. As previously indicated the motion of the paper sheet 16 is set up so that as it traverses a paper making machine (not shown) it would be directly out of FIG. 1 toward the reader. The combination of this motion of the paper with the disposition of the waveguides across the sheet produces the sampling pattern. The waveguides have several advantages over normal scanning in that they assure that the light beam arrives at the paper sheet at normal incidence. This normal incidence produces the simplest measurements and also the simplest calculation procedures. The waveguides 80–85 also serve to isolate the laser beam during most of its trajectory from the dust particles and elevated air moisture of a factory environment in which this type of device would be utilized.

The portion of the laser beam from each of the waveguides which passes through the paper after leaving each of the waveguides is detected by the series of detectors $D_3$ which are variously labelled as detectors 90–95. Each of the detectors 90–95 contains two individual detector units and is of the same construction with the detector 90 being shown in the FIG. 1 in detail. Radiation from the waveguide 80 which passes through the paper sheet 16 is passed through the beam splitter 71 and, by one path to the detector unit 51 while by another path to the detector unit 53 by way of the mirror 72. In a manner similar to the detectors 45 and 46 each of the detectors 51 and 53 have preceding them filters 60 and 61 which respectively filter out the first and second wavelength in order to ensure that one of the detectors receives the first wavelength and the other of the detectors receives the second wavelength transmission. The outputs from the detectors 51 and 53 and subsequently the outputs from each of the other detectors 91–95 is fed to the microcomputer 40. This output from the detectors 90–95 provides for information with respect to the amount of energy transmitted through the paper to the detectors. Using this transmitted energy presented in quantitative form by the detectors and subsequent well known circuitry, the microcomputer proceeds to calculate the transmittance and correlate the transmittance with the position at which the measurement was made. Transmittance is defined as the ratio of the transmitted intensity to the incident intensity; i.e., it is the ratio of the signals detected by the detectors 90–95 and the detectors 45 and 46 respectively, for each of the wavelengths. The detectors 45 and 46 and the detector units 51 and 53 for each detector section 90–95 are pyroelectric detectors which are commercially available and are formatted as either a single element or in arrays. Other appropriate detectors may be used.

The above defined apparatus will now be discussed with respect to measurements necessary to provide the water content and basis weight of the paper sheet 16. The basis weight of a paper sheet is defined as the mass per unit area. If water is present the basis weight has two components; $x_f$=fiber mass/area and $x_w$=water mass/area. The moisture percentage is defined as $P_w = X_w/(X_w+X_f)$. $P_w$ and $X_f$ are parameters of primary importance in the manufacturing and characterization of paper. Experimental data show that the transmittance at wavelength $\lambda$, which is called $T(\lambda)$ is related to $P_w$ by the formula:

$$-\ln T(\lambda) = a(\lambda) + b(\lambda)P_w$$

This formula was derived from data obtained by utilizing

For any given wavelength and dry basis weight, a and b are constants. In addition to being a function of $\lambda$, $a(\lambda)$ also varies with the dry basis weight $x_f$; however, $b(\lambda)$ does not vary. $a(\lambda)$ and $b(\lambda)$ are determined by calibration measurements. If $x_f$ does not vary, i.e., if the fiber mass per area does not change, then $P_w$ is determined from the above formula for $T(\lambda)$.

Experimental measurement indicates that, when $x_f$ changes because the thickness of the paper changes while its density remains constant, then $a(\lambda)=c(\lambda)x_f$.

At a given wavelength, c is a constant which can also be determined from calibration measurements.

A combination of the above three equations for $P_w$, $T(\lambda)$ and $a(\lambda)$ yields the following quadratic equation in $x_f$:

$$x_f^2 + \left|\frac{c(\lambda)x_w + \ln T(\lambda)}{c(\lambda)}\right|x_f + \left|\frac{b(\lambda) + \ln T(\lambda)}{c(\lambda)}\right|x_w = 0 \quad (1)$$

If the measurements are made at two different submillimeter wavelengths, equation (1) can be applied to each of them, and the resulting pair of simultaneous equations can be solved for $x_f$ and $x_w$. The results can be expressed in the following form $$x_f = \frac{b(\lambda_1)\ln T(\lambda_2) - b(\lambda_2)\ln T(\lambda_1)}{c(\lambda_1)b(\lambda_2) - c(\lambda_2)b(\lambda_1)}$$

$$x_w = x_f\left|\frac{c(\lambda_1)x_f + \ln T(\lambda_1)}{c(\lambda_1)x_f + \ln T(\lambda_1)} + b(\lambda_1)\right| =$$

$$-x_f\left|\frac{c(\lambda_2)x_f + \ln T(\lambda_2)}{c(\lambda_2)x_f + \ln T(\lambda_2)} + b(\lambda_2)\right|$$

The value of each of these quantities, and hence of $P_w$ as well, can be calculated and stored continuously as the laser beam scans the paper sheet. Measurements at additional wavelengths can be used, if desired, to enhance measuremental precision. If $X_f$ changes for reasons other than a change in the sheet thickness the equation $a(\lambda)=c(\lambda)x_f$ may assume a slightly different form but the principle on which the calculations are based will not change.

The selection of the use of submillimeter lasers for the measurements is based upon the consideration that dielectric materials such as paper are quite transparent in the submillimeter range of the electromagnetic spectrum which is defined within the range of about 50–1000 microns. This particular spectral region is characterized by strong absorption with a strong but simple wavelength dependency. Thus, the transmittance of submillimeter waves through various thicknesses of paper is very sensitive to small amounts of water.

Figure 2:
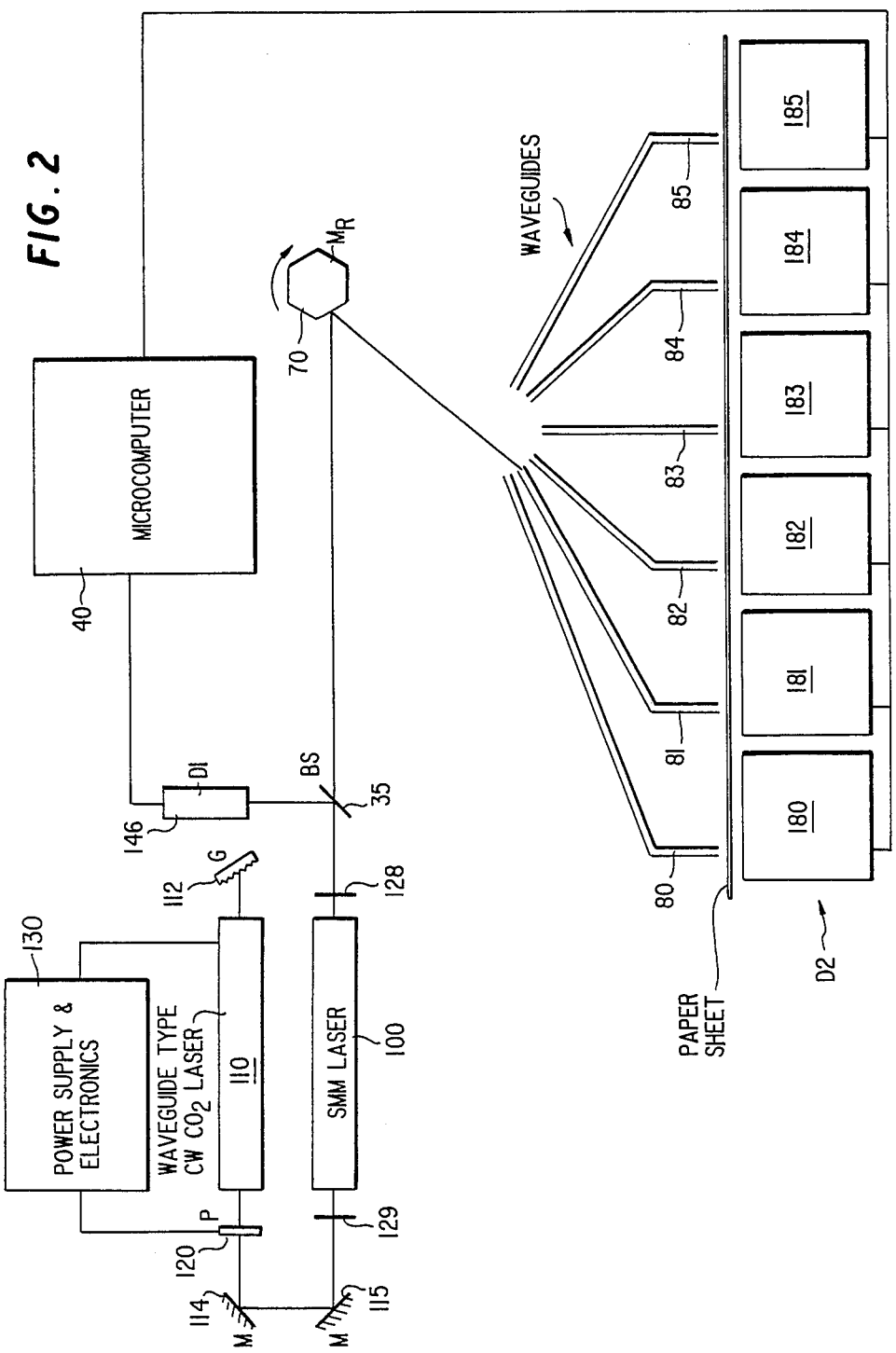
FIG. 2 illustrates a second embodiment featuring an alternate apparatus for generating the wavelengths used in the measurement of moisture and basis weight of paper.

Another embodiment for generating submillimeter waves at two different wavelengths is illustrated in FIG. 2 which can generate two different wavelengths by utilizing a single SMM laser 100 which is equivalent to either of the SMM lasers 20 and 30 of FIG. 1 and which contains hybrid mirrors 128, 129 which is also equivalent to the hybrid mirrors 28, 29, 38 and 39 of FIG. 1. The primary difference in the FIG. 2 embodiment, which permits the utilization of a single SMM laser 100, is the use of a waveguide type CW (continuous wave) $CO_2$ laser 110 which is a specialized laser which, acting in conjunction with the piezoelectric mirror displacer 120 can provide two wavelength outputs. These two wavelength outputs alternate in time with the piezoelectric displacer 120 acting as a time switch to switch the laser output from the waveguide laser 110 at 2 separate wavelengths. It is to be noted that this piezoelectric displacer 120, which acts as a switch, is different from the optical couplers 13 and 23 in the FIG. 1 embodiment. Those optical couplers 13 and 23 merely serve to stabilize a chosen frequency which frequency was chosen by the movement of the diffraction gratings 12. In this embodiment of FIG. 2 when the diffraction grating 112 is set to choose a particular output line from the laser, the piezoelectric displacer provides such a tuning that two separate wavelengths are generated, alternating in time.

One of the key features concerning the FIG. 2 embodiment is obvious from a comparison of the Figures. That is, there is no longer a need for two separate sets of laser configurations and furthermore the beam splitter 47 in FIG. 1 as well as one of the detectors 46, 45 can be eliminated. Likewise, the configuration with respect to the detectors for detecting the transmission of light through the sheet paper 16 can consist of a series of single detectors 180–185 which can be set to sample at a frequency corresponding to the frequency at which the resonator mirror 120 provides an output at a first wavelength and then at a second wavelength. The same type of control for the detectors 180–185 can be used to provide for alternate detection of wavelengths for the detector 146 in the FIG. 2 embodiment. The remaining structure with respect to FIG. 2 is identical with that of FIG. 1 with the exception of the power supply and control portion 130 which must control the resonator 120. It should also be noted that in fact the resonator 120 can be mounted on a piezoelectric crystal which is the same as the piezoelectric crystal discussed in the embodiment of FIG. 1 for the couplers 13 and 23, however, the control and its interaction between the laser outputs from the lasers 10 and 26 are vastly different than that shown in the FIG. 2 embodiment with respect to the specific waveguide continuous wave laser 110. Once again it is also indicated that the detectors, although utilizing but a single detector for each section 180–185, must be controlled so as to sample alternately at two different frequencies whereby the alteration between the sampling in time corresponds to the alternation which occurs between the first wavelength output from the laser 100 and the second wavelength output from the laser 100. This is of course under the control of the microcomputer 40 and the provision of this time sampling of the detectors 180–185 and 148 is well known.

The present invention thus provides for a realtime, on-line measurement of the moisture content and basis weight of a paper sheet at various stages of its manufacture. The system which utilizes the production of two separate submillimeter wavelength outputs from submillimeter lasers produces a high-resolution spatial profile of both the basis weight and the moisture content over a wide range of moisture content and over a wide range of thickness of paper stock. The system is able to be utilized in conjunction with the production of high speed paper feeding and can provide for scanning over the entire width of a large paper sheet which is moving at a rapid rate, as is common in the paper industry. The information produced by the simultaneous determination of basis weight and moisture content over a wide range can be used for optimization of the paper production process in terms of energy consumption, for example, and to control the quality of the products. The system in both embodiments overcomes the prior art problems with respect to microwave and infrared moisture gauges in that it can produce a directed beam which can be steered to provide for scanning and in that it offers improvements in speed, accuracy, spatial resolution, range of moisture content which can be measured, and range of dry stock which can be accomodated.

Obviously, numerous (additional) modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A system for simultaneous determination of moisture content and basis weight of paper, comprising:
    laser means for producing a beam having at least a first and a second wavelength of submillimeter wavelength radiation;
    means for scanning said beam across the width of said paper;
    detector means positioned opposite said paper from said beam for receiving the portion of said scanning beam which is transmitted through said paper and for outputting transmittance signals for each of said at least first and second wavelengths; and
    processing means for receiving said transmittance signals for each of said first and second wavelengths and for calculating and outputting an indication of the moisture content and basis weight of said paper.

2. The system according to claim 1, wherein said laser means comprises two submillimeter lasers wherein the water content and basis weight of said paper is measured simultaneously and continuously in real time.

3. The system according to claim 1, wherein said laser means comprises a single submillimeter laser and a means for alternating the wavelength of said single submillimeter laser between two preselected values wherein the water content and basis weight of said paper is measured simultaneously and at a sampling rate determined by said detector means.

4. The system according to claim 2, further comprising a continuous wave $CO_2$ laser which pumps said two submillimeter lasers in order to produce said first and said second wavelengths.

5. The system according to claim 3, wherein said means for alternating the wavelength of said single submillimeter laser includes a piezoelectric crystal tuned resonator in order to provide said first and said second wavelengths which are output in a single beam of said single submillimeter laser.

* * * * *